United States Patent
Lauf et al.

(10) Patent No.: US 7,135,288 B2
(45) Date of Patent: Nov. 14, 2006

(54) COMBINATORIAL SYNTHESIS OF CERAMIC MATERIALS

(75) Inventors: Robert J. Lauf, Oak Ridge, TN (US); Claudia A. Walls, Oak Ridge, TN (US); Lynn A. Boatner, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 677 days.

(21) Appl. No.: 10/256,549

(22) Filed: Sep. 27, 2002

(65) Prior Publication Data
US 2004/0062911 A1    Apr. 1, 2004

(51) Int. Cl.
*C12Q 1/68* (2006.01)
*C12Q 30/10* (2006.01)
*C40B 50/08* (2006.01)

(52) U.S. Cl. .......................... 435/6; 264/109; 264/119; 264/655; 264/669; 264/678; 419/44

(58) Field of Classification Search ...................... None
See application file for complete search history.

(56) References Cited

U.S. PATENT DOCUMENTS

| | | | |
|---|---|---|---|
| 5,143,854 A | 9/1992 | Pirrung et al. | |
| 5,776,359 A | 7/1998 | Schultz et al. | |
| 5,941,728 A | 8/1999 | Okabe et al. | |
| 5,959,297 A | 9/1999 | Weinberg et al. | |
| 5,985,356 A | 11/1999 | Schultz et al. | |
| 6,004,617 A | 12/1999 | Schultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,151,123 A | 11/2000 | Nielsen | |
| 6,182,499 B1 | 2/2001 | McFarland et al. | |
| 6,187,164 B1 | 2/2001 | Warren et al. | |
| 6,228,299 B1 | 5/2001 | Janney et al. | |
| 6,248,286 B1 | 6/2001 | Lauf et al. | |
| 6,248,540 B1 | 6/2001 | Weinberg et al. | |

OTHER PUBLICATIONS

Janney et al. "Development of Low-Toxicity Gelcasting Systems" J. Am. Ceram. Soc. 1998, 81(3), 581-591.*
J. H. Claassen et al, "A Contactless Method for Measurement of the Critical Current Density and Critical Temperature of Superconducting Films," Rev. Sci. Instrum.. vol. 62 (No. 4). Apr. 1991.
http://www.theva.com/home/home.html.

* cited by examiner

*Primary Examiner*—Jon Epperson
(74) *Attorney, Agent, or Firm*—Joesph A. Marasco

(57) ABSTRACT

A combinatorial library includes a gelcast substrate defining a plurality of cavities in at least one surface thereof; and a plurality of gelcast test materials in the cavities, at least two of the test materials differing from the substrate in at least one compositional characteristic, the two test materials differing from each other in at least one compositional characteristic.

30 Claims, 4 Drawing Sheets

COMBINATORIAL SYNTHESIS OF CERAMIC MATERIALS

The United States Government has rights in this invention pursuant to contract no. DE-AC05-00OR22725 between the United States Department of Energy and UT-Battelle, LLC.

FIELD OF THE INVENTION

The present invention relates to methods for preparing libraries of distinctive compositions for screening of various properties thereof, and more particularly, to the use of gelcasting techniques to prepare a library of distinct bulk compositional zones disposed in or on a substrate for measuring of various properties thereof.

BACKGROUND OF THE INVENTION

The number of candidate compositions is nearly infinite for various useful materials, such as superconductors, zeolites, magnetic materials, phosphors, nonlinear optical materials, thermoelectric materials, high and low dielectric materials and the like. Discovery and optimization of such compositions is not trivial. Even though the chemistry of extended solids has been extensively explored, few general principles have emerged that allow one to predict with certainty the composition, structure and reaction pathways for the synthesis of such solid state compounds.

The preparation of new materials with novel and useful chemical and/or physical properties is at best unpredictable considering current levels of understanding. Consequently, the discovery of new materials depends largely on the ability to synthesize and analyze new compounds. Given approximately 100 elements in the periodic table, which can be used to make compositions consisting of three, four, five, six or more elements, the universe of possible new compounds remains largely unexplored. As such, there exists a need in the art for a more efficient, economical and systematic approach for the synthesis of novel materials and for the screening of such materials for useful properties.

Using the techniques of "combinatorial chemistry", methods have been developed for the synthesis and screening of large libraries (up to $10^{14}$ molecules) of peptides, oligonucleotides and other small molecules. Using various state-of-the-art methods, arrays containing thousands or potentially millions of different combinations of elements can be formed. Such techniques have met with substantial success in, for example, screening various ligands such as peptides and oligonucleotides to determine their relative binding affinity to a receptor such as an antibody.

Methods of combinatorial synthesis involve substrates supporting arrays of diverse materials in predefined regions. A substrate having an array of diverse materials thereon is generally prepared by delivering components of materials to predefined regions on the substrate to form different materials. Many classes of materials can be generated combinatorially, including, for example, inorganic materials, intermetallic materials, metal alloys, ceramic materials, etc. Once prepared, such materials can be screened for useful properties including, for example, electrical, thermal, mechanical, chemical, etc. Arrays of materials with slightly varying composition, concentrations, stoichiometries and thicknesses are deposited on known locations on a substrate so that the materials can be readily synthesized and analyzed.

It will be appreciated that methods of combinatorial chemistry described to date suffer from an inherent limitation, viz., that they are mainly suited for screening materials whose intended use will be in the form of a thin film rather than a "bulk" form. Sample arrays fabricated by thin-film deposition methods cannot replicate crucial processing steps used to make bulk materials (casting, sintering, cold or hot rolling, etc.) Moreover, it is very difficult to measure many crucial properties, especially mechanical properties, in a small region on a much larger substrate and have reasonable confidence that the true properties of such a small volume of material are actually being obtained.

OBJECTS OF THE INVENTION

The present invention is intended to overcome at least some of the above described limitations, by making it possible to fabricate, in one test specimen, a large number of compositionally distinct regions while preserving crucial aspects of "bulk" processing. Examples will be shown that describe how the technique can be applied to, for example, emissive refractories, structural ceramics, ionic conductors, and catalysts.

Some objects of the present invention include the following:

1. Rapidly prepare a large number of ceramic compositions for evaluation or other purposes while preserving aspects of bulk material processing.

2. Rapidly create a combinatorial library of compositions whose microstructure and properties are representative of materials made one at a time.

3. Create a combinatorial library in which each composition is represented by a substantial volume of material rather than simply a surface spot.

4. Allow for the interaction or intermixing of deposited material with the "substrate" to create virtually infinite gradations of composition and properties.

5. Create a combinatorial library of samples of sufficient size and shape to measure transport properties, including ionic conductivity.

Other objects and advantages will be accomplished by the present invention, which is designed to create a monolithic sample of ceramic material containing distributed discrete volumes of modified compositions for property evaluation. The method of the present invention is distinguished from prior combinatorial chemistry methods by its ability to create volumes of material (rather than thin surface films) and to replicate bulk ceramic processing, whereby realistic microstructures and physical properties are obtained.

Further and other objects and advantages of the present invention will become apparent from the description contained herein, read together with the attached drawing.

SUMMARY OF THE INVENTION

In accordance with one aspect of the present invention, the foregoing and other objects are achieved by a method of preparing a test article having an array of inorganic compositions including the steps of: providing a green gelcast substrate defining a plurality of cavities in at least one surface thereof, depositing test slurries into at least two of the cavities, each of the test slurries comprising at least a powder, a solvent, and a polymerizable monomer, at least two of the test slurries differing from the substrate slurry in at least one compositional characteristic, the two test slurries differing from each other in at least one compositional characteristic; and polymerizing the monomer in the test slurries in the cavities to form a plurality of test materials in the cavities, at least two of the test materials differing from the substrate in at least one compositional characteristic, the two test materials differing from each other in at least one compositional characteristic.

In accordance with another aspect of the present invention, a combinatorial library includes a gelcast substrate defining a plurality of cavities in at least one surface thereof; and a plurality of gelcast test materials in the cavities, at least two of the test materials differing from the substrate in at least one compositional characteristic, the two test materials differing from each other in at least one compositional characteristic.

BRIEF DESCRIPTION OF THE DRAWING

Like features in the drawing are identified by like numerals.

Figure 1:
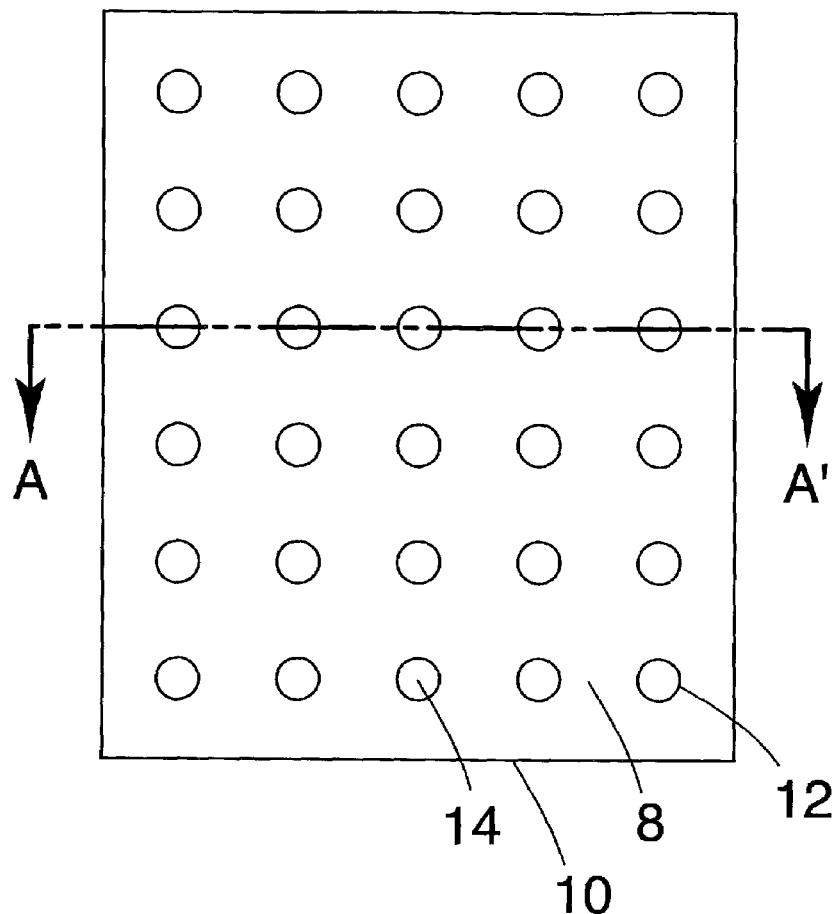
FIG. 1 illustrates a top view of a ceramic substrate defining an array of discrete volumes of test materials of distinctive compositions in accordance with the present invention.

For a better understanding of the present invention, together with other and further objects, advantages and capabilities thereof, reference is made to the following disclosure and appended claims in connection with the above-described drawings.

DETAILED DESCRIPTION OF THE INVENTION

The present invention involves combinations of well-known processes and materials in new ways to create tests objects having libraries of chemical combinations in substantially homogeneous "bulk" structures.

In some embodiments, the present invention exploits the fact that certain gelcasting formulations lend themselves to green machining in the dry state. In some embodiments, the present invention exploits the well-known property of reversible hydrogels to take up solvent and thereby expand into their previous size and shape. The present invention further exploits the property of gelcasting that gelation occurs at constant volume. The present invention can also make use of aspects of recently demonstrated methods to make functionally graded materials by gelcasting. For example, see, U.S. Pat. No. 6,248,286 issued on Jun. 19, 2001 to Lauf et al., the entire disclosure of which is incorporated herein by reference.

In general terms, a wet gelcast body (substrate) is formed in which a number of cavities are distributed across at least one surface. Test slurries (slurries comprising test materials), which can be similar to the substrate composition but with systematically varied additives or modifiers, are deposited into the cavities and gelled. The substrate with cavities containing gelled test materials is subsequently dried and sintered, resulting in a test article that contains a combinatorial library of bulk test material compositions that are suitable for evaluation.

Some examples of the sundry and various materials systems for which the present invention is suitable are the following: structural ceramics; silicon nitride; solid electrolytes and oxygen membranes; emissive materials; refractories; ferrites; dielectrics; varistors; catalytic materials; zirconia; high temperature superconductors; scintillators; phosphors; dosimeter materials; radiation resistant ceramics; and luminescent materials such as cathodoluminescent materials and display materials.

Some examples of the sundry and various properties and/or characteristics that can be used in conjunction with the present invention to screen combinatorial libraries include: optical properties, including emissivity and superemissivity; magnetic permeability; dielectric permittivity; loss tangent; microstructural features such as, for example, grain size, grain shape, and grain boundary phases; microhardness; surface catalytic activity; biological activity such as, for example, thrombogenicity and osteoinduction; corrosion or oxidation resistance; luminescence, cathodoluminescence and scintillation.

It is well known in the art that gelcasting is an adaptable process that can be modified in various ways to accommodate particular applications. For example, both aqueous and nonaqueous systems have been developed and used, along with a variety of monomers and combinations thereof. Plasticizers such as polyethylene glycol (PEG) may be added to modify the drying characteristics of the wet green body, and rehydration characteristics and mechanical properties (for example, toughness and machinability) of the dried green body. For example, see, U.S. Pat. No. 6,228,299 issued on May 8, 2001 to M. A. Janney et al., the entire disclosure of which is incorporated herein by reference.

A key aspect of the invention relies on a wet gelled body (substrate) having a number of cavities distributed in an array across at least one surface, into which compositionally modified slurries are deposited and gelled, resulting in an array of discrete and variable test materials. The cavities can be made by either of two methods, direct-casting and green-machining, as described hereinbelow.

Figure 2:
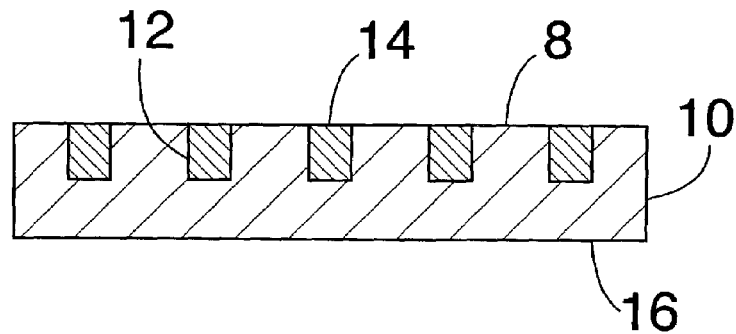
FIG. 2 is a cross section through A, A' of FIG. 1, illustrating an embodiment of the present invention having "blind" volumes of test materials that do not penetrate all the way through the substrate.
Figure 3:
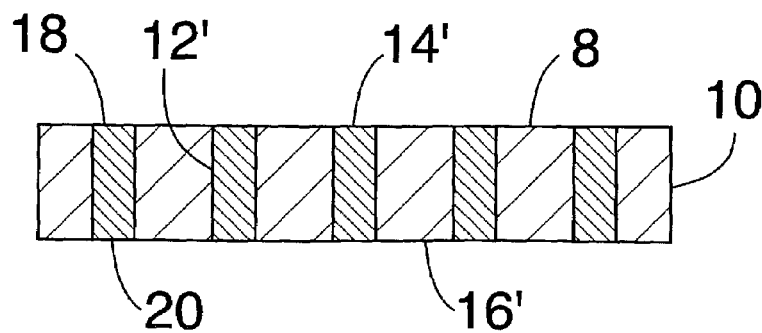
FIG. 3 is a cross section through A, A' of FIG. 1, illustrating an embodiment of the present invention having volumes of test materials that penetrate all the way through the substrate.

FIG. 1 shows a simple embodiment of the invention. A substrate 10 can be a plate, block, cylinder, or a body of any suitable shape and size. In at least one surface 8 thereof, cavities 12 contain test materials 14. Shape of the cavities 12 can be varied as desired, for example, wells and/or channels, etc. Depth of the cavities 12 can also be varied as desired, from very shallow to very deep. FIG. 2 is a cross section through A, A' of FIG. 1, illustrating an embodiment of the present invention having "blind" volumes of test materials that do not penetrate all the way through the substrate. FIG. 3 is a cross section through A, A' of FIG. 1, illustrating an embodiment of the present invention having volumes of test materials that penetrate all the way through the substrate.

In a direct-casting method, cavities are cast directly into the substrate using a mold that has, for example, pins protruding from at least one surface. After gelation the body is removed from the mold and is immediately ready for modified slurry compositions to be poured into the cavities. The direct-casting method has at least the following advantages: fewer process steps; machining equipment is not needed; drying and rehydration times are eliminated. The direct-casting method may also have disadvantages relative to a green-machining method described hereinbelow: separate hard tooling must be made for each desired pattern of cavities; molding is more difficult and yields will decrease as the number of cavities increases or their spacing decreases.

In a green-machining method, a simple shape, for example, a rectangular plate, may be gelcast and dried. Cavities are subsequently machined into the dry substrate by drilling, milling, or the like, after which the body is rehydrated to the wet gel state to receive the modified slurries. The green-machining method has at least the following advantages: a large number of simple plates can be cast and dried for easy storage and long shelf life; size and shape of cavities may be easily changed without having to create new hard tooling; small, closely spaced cavities can be drilled reliably with minimal scrap. The green-machining method may also have disadvantages relative to a direct-casting method described hereinabove: more process steps; and the time needed to dry and then rehydrate the gel.

Any method that produces a gelcast substrate having cavities therein which are subsequently at least partially filled with test materials is contemplated to fall within the scope of the present invention.

The skilled artisan can easily select which of the foregoing methods is most suitable for a particular application based on straightforward engineering principles such as the desired number of cavities per sample and the total number of samples to be made of a particular base composition. The optimal number, dimensions, shape, and spacing of substrates and cavities defined thereby depends to some degree on the methods to be used to evaluate the properties of interest, since, for example, some measurements will naturally require a greater or lesser volume of material than others to produce representative data.

For some applications it is desirable to have discrete volumes of material of well-defined compositions that are preselected as part of a systematic or factorial experiment. In this situation, the cavities are well spaced to minimize interdiffusion of species between the different volumes, as shown in FIGS. 1–3. It will be understood that some interdiffusion will take place at the interface of material in each well and the substrate matrix. Therefore, the size of each well must be selected to provide a sufficient volume of reasonably homogeneous material for testing, taking these "edge effects" into account.

Figure 7:
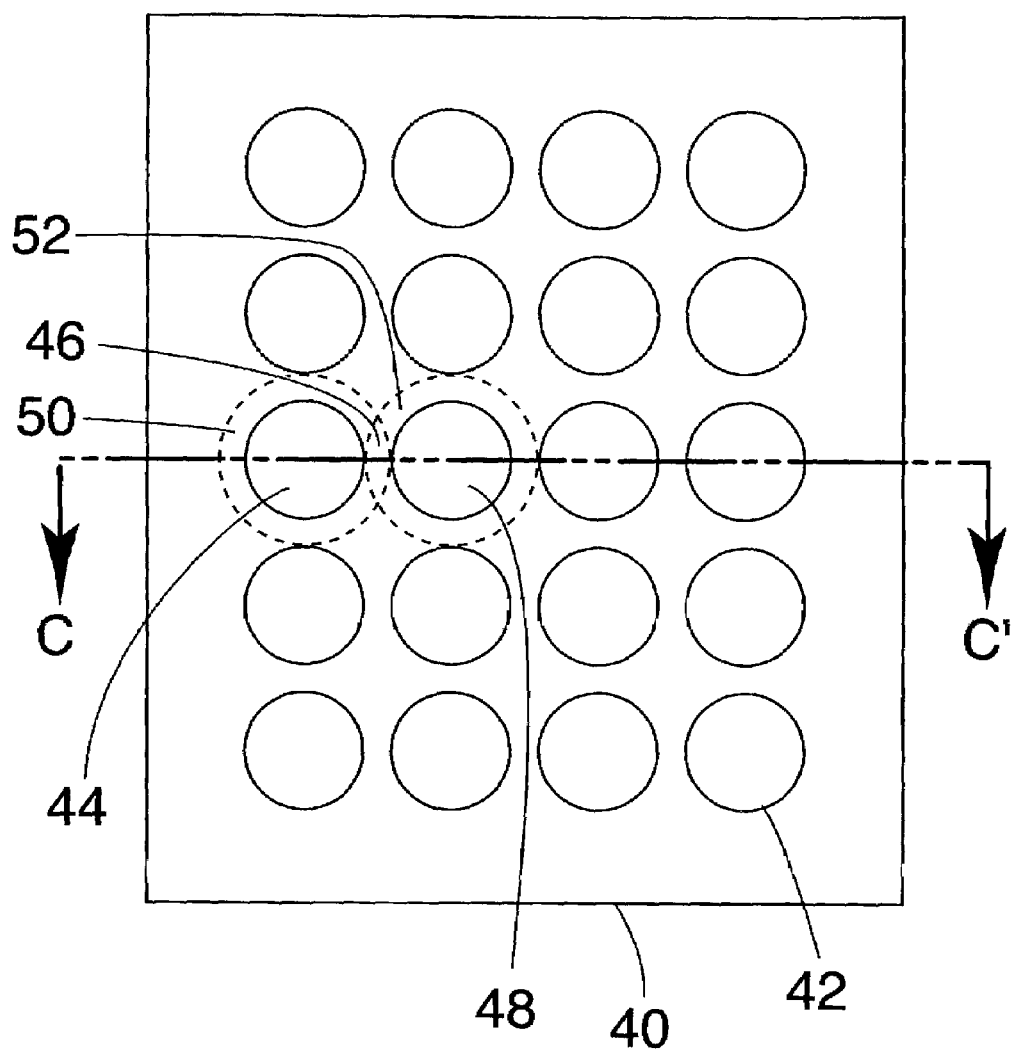
FIG. 7 illustrates a top view of a ceramic substrate defining an array of discrete, closely spaced volumes of test materials of distinctive compositions in accordance with the present invention.

Referring now to in FIG. 7, 8, a substrate 40 defines an array of cavities 42 which contain test materials 44, 48. In some embodiments of the present invention, test materials 44, 48 diffuse to a desirable degree into the surrounding substrate during processing to form respective regions of diffusion 50, 52 within the substrate 40.

Figure 8:
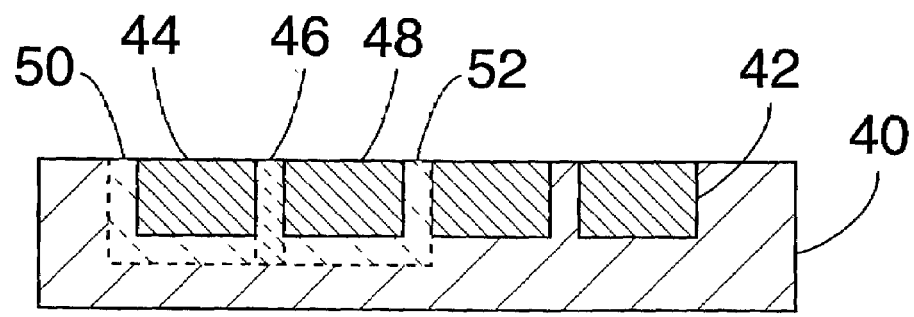
FIG. 8 is a cross section through C, C' of FIG. 7.

Moreover, in some embodiments of the present invention, such as is shown in FIGS. 7, 8, the cavities may be placed more closely together to allow a desired degree of interdiffusion of test materials. Regions of interdiffusion 46 can form between regions of diffusion 50, 52 of adjacent test materials 44, 48 within the substrate 40. By allowing diffusion and interdiffusion, and to any desired degree, a continuum of compositions across the sample can be achieved. Properties may be evaluated in regions of undiffused, diffused, and interdiffused test materials at many locations. Where desirable properties are found the material is analyzed to determine the exact composition corresponding to the desirable properties.

U.S. patent application Ser. No. 09/935,852 filed Aug. 23, 2001 by Lowden et al., the entire disclosure of which is incorporated herein by reference, describes the utility of refractory ceramics based on yttrium aluminum garnet (YAG) and related compounds, doped with rare earth elements to provide superemissivity in selected spectral ranges. It is noted therein that a very large number of dopants, alone or in combination, could be used to create many different emission lines. The present invention may be used to prepare arrays of test materials in accordance therewith.

EXAMPLE I

Yttria and alumina powders were blended in the correct molar ratio to yield YAG ($Y_3Al_5O_{12}$) upon sintering. A slurry containing 50% solids was prepared as follows:

256.76 g $Y_2O_3$=51.352 ml
193.24 g $Al_2O_3$=48.553 ml
4.5 g Darvan 821A (40% solution in the bottle)
80.5 ml Deionized Water
11.25 gMBAM
3.75 g PEG(1000)DMA
0.10 μl TEMED and 1.0 μl 10% APS per 1 gram weight of slurry The mixture was ball milled overnight using 200 grams of media in a 1 liter mill. The mixture was cast into a rectangular plate using standard gelcasting procedures and dried. Cavities were drilled into this plate extending to about half its thickness. The drilled plate (substrate) was then gradually rehydrated to its original gelcast state. The substrate was first set on a flat support above a volume of water in a closed container and allowed to stand overnight. The next day the entire assembly was gradually heated to 50° C., held overnight, then further heated to 75° C. and held overnight, after which the substrate was immersed in water to complete the rehydration process.

EXAMPLE II

Figures 9, 10:
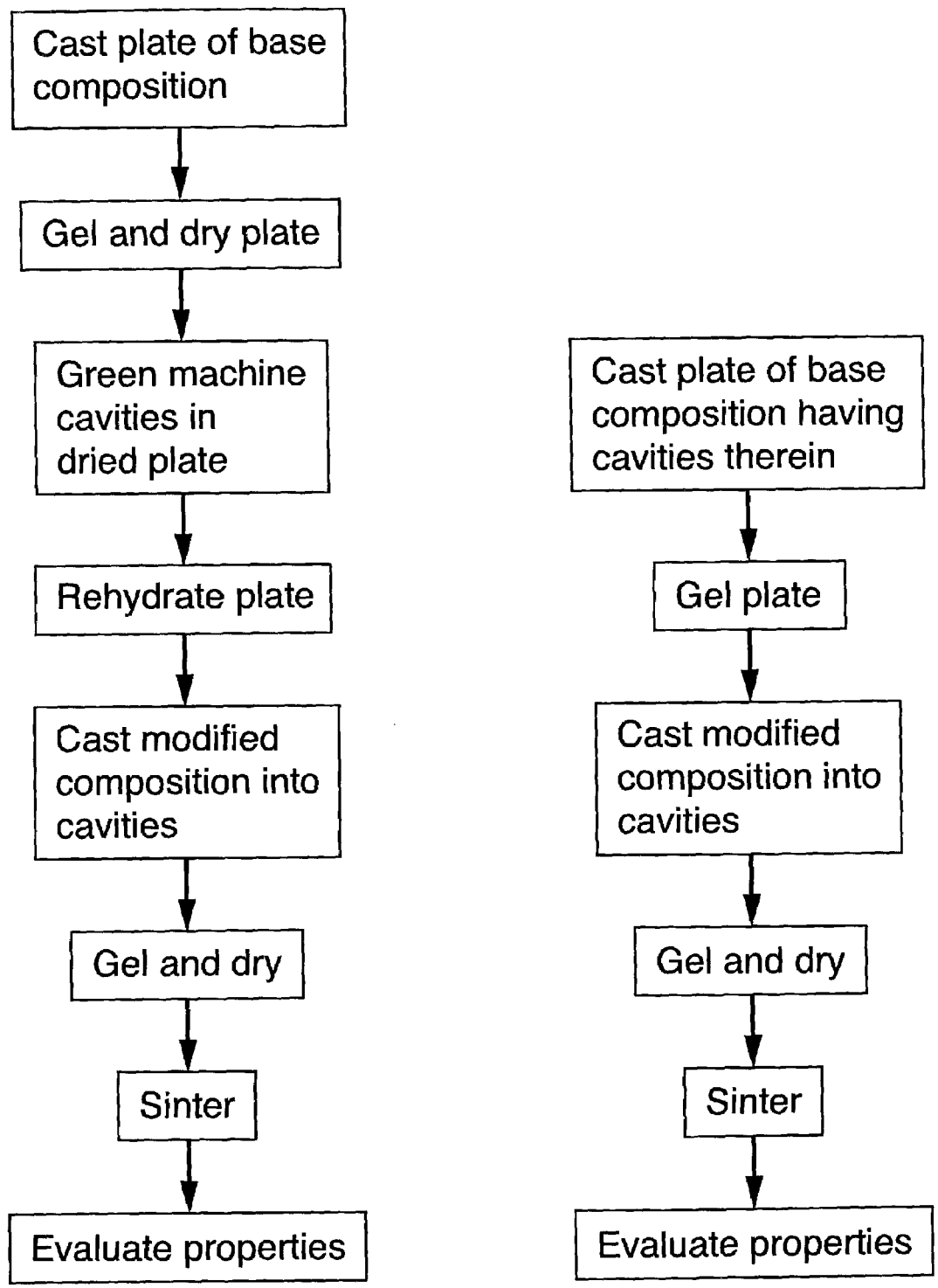
FIG. 9 is a flow diagram of a process for carrying out an embodiment of the present invention wherein cavities are created in the substrate by green machining.
FIG. 10 is a flow diagram of a process for carrying out an embodiment of the present invention wherein cavities are formed directly during the casting process.

Slurry prepared as described in Example I is modified by the addition of selected combinations and amounts of rare earth elements and deposited into the cavities of a substrate prepared in accordance with Example I. The substrate is then heated to cause the newly introduced slurries to gel, after which the substrate with deposited materials is dried again and fired to form a solid test plate having an array of zones of distinct compositions. The general sequence of process steps is shown in FIG. 9.

Rehydration may be accelerated when the slurry has been modified by the addition of plasticizers. The use of plasticizers is taught generally in U.S. Pat. No. 6,228,299 issued on May 8, 2001 to Janney, et al., incorporated herein by reference. Plasticizers may be added as desired in any suitable concentration; the addition of plasticizers is not critical to the practice of the present invention. As a general example, a conventional 100 g gelcasting premix solution with 15% monomer mix might contain 85 g water and 15 g monomers. A plasticized mix would contain 82.75 g water, 15 g monomers, and 2.25 g plasticizer (typically PEG 400 or glycerin). The addition of plasticizer keeps the substrate from over-drying and malforming or rending the gel, and also assists in machinability.

The development of ferrites and dielectrics has traditionally been done empirically. Using the present invention, a "base" ferrite composition can be cast into a substrate and machined, after which modified ferrite slurries can be distributed among the various cavities.

EXAMPLE III

A substrate is prepared as described in Example I containing:
 904.0 g CN-20 Ni—Zn ferrite powder 500° C. (calcined to remove binders)
 2.68 ml Darvan 821A (40% solution in the bottle)
 142.55 ml Deionized Water
 21.56 g MBAM
 3.59 gMAM
 0.15 µl TEMED and 1.5 µl 10% APS per 1 gram weight of slurry.

Test slurries are deposited into the cavities of the substrate and a test plate is prepared as described in Example II. The test plate, with its resulting range of compositions, can be interrogated with a small sensing coil to determine local magnetic properties. Small areas having some desired combination of properties could subsequently be analyzed by microprobe or the like to determine the actual composition that gives the desired properties.

The importance of piezoelectric transducers and actuators for applications in a wide range of systems that encompass military, commercial, and medical applications is constantly increasing. New applications that are being developed and envisioned continue to place more restrictive and strenuous demands on the performance characteristics of piezoelectric materials. The discovery, development, and optimization of new piezoelectric materials require synthesis and testing of bulk mixed-phase ceramic materials on a numerically large scale. Accordingly, a combinatorial fabrication and testing system of the type described in the present invention can be used to significantly enhance and improve the efficiency of the process of discovering and optimizing new piezoelectric actuator and transducer materials. The present invention is ideally suited to the synthesis and screening of the required suite of bulk ceramic specimens of multi-component piezoelectric materials.

Silicon nitride structural ceramics contain numerous sintering aids to control grain size, microstructural development, grain boundary phases, creep behavior, etc. Prior work has established a good knowledge base on gelcasting formulations for silicon nitride systems.

EXAMPLE IV

A Silicon Nitride substrate containing 45% solids is prepared as follows:
 900 g E-10 $Si_3N_4$ (Ube)
 50 g $Y_2O_3$ (Molycorp)
 50 g $Al_2O_3$ RCHP-DBM w/0.05 wt. % MgO (Reynolds)
 25 PVP K-15 (20% solution in Water)
 12 ml Darvan 821A (40% solution in the bottle)
 286 ml Deionized Water
 7.2 g MBAM
 43.3 gMAM
 2 ml of10 wt. % AZIP After turbo-milling, this slurry is de-aired and used to prepare a substrate as described in Example I.

Using the method described in Example II, a test plate having a combinatorial library is prepared. The combinatorial library contains a large number of variants of modified silicon nitride. Each variant is subsequently analyzed to determine key properties such as microhardness, localized fracture toughness (for example, using the indentation method), grain size and morphology (for example, by SEM examination), etc.

It will be understood that in some cases, further processing might be desirable to facilitate and/or enhance accurate and/or precise testing. Some examples of further processing operations include grinding, polishing, etching, etc., as are well known in the art of ceramic sample preparation.

The present method creates a volume of material that is sufficient to perform indentation fracture toughness measurements (for example, 3 mm diameter by 3 mm deep) whereas conventional thin-film combinatorial methods are not generally suitable for such testing.

Test articles made by the present invention can also be subjected to air or steam corrosion, for example, and subsequently examined afterward to determine the corrosion rate, degree of surface passivation, degree of surface protection, etc. in the different compositional zones. It will be appreciated that this method would greatly reduce the cost of performing exposure or corrosion testing relative to using a like number of full-sized samples and will easily allow the side-by-side comparison of the performance of many compositions under the same environment.

FIG. 3 illustrates an embodiment of the present invention that would be suitable particularly for evaluating solid electrolytes, oxygen membranes, and other materials where one would like to measure actual bulk transport properties. The cavities 12' and test materials 14' deposited therein extend all the way through the substrate 10. The through-cavities 12' can be formed by either the direct-casting or the green-machining method. A wet gel body can be made with cavities 12' running completely through its thickness, held flush against a plate, rubber gasket, or other appropriate conventional stopping means while adding slurries to the cavities 12', and removed from the gasket surface after the modified compositions have gelled therein.

In some cases, it may be preferable to fabricate a test article as illustrated in FIG. 2 and subsequently machine away the bottom surface 16 thereof to expose the test materials 14 and thus have a final test article similar to that shown in FIG. 3, where the bottom surface 16' has exposed test materials 14'.

EXAMPLE V

A test article is prepared according to Example I and Example II. The top surface 8 is ground only to assure that it is adequately smooth, whereas the bottom surface 16 is ground far enough to remove sufficient substrate 10 material so that the test materials 14 extend completely through the thickness of the sample plate. Electrodes are disposed on the opposing surfaces of each and tests are performed thereon for transport properties, dielectric strength, and other parameters of interest.

The structure shown in FIG. 3 also lends itself to rapid or parallel analysis of some transport properties, particularly thermal conductivity. The bottom surface 16' of a test article may be placed on a heated or chilled surface while mapping the temperature distribution on the top surface 8 using well-known thermal imaging techniques. Similarly, the catalytic properties of a large combinatorial library of the present invention may be simultaneously evaluated by observing the entire plate with an infrared imaging camera while exposing the plate to an appropriate gas mixture to highlight the most catalytically active (hot) regions. Emissivity and superemissivity may be similarly measured over any appropriate spectral range.

It is well known that the properties of certain materials such as ferroelectrics and piezoelectrics are improved by "poling" in which the sample is subjected to an electric field while cooling through its Curie temperature. By applying electrodes to the top 18 and bottom 20 surfaces of the test materials 14', all of the individual sample volumes may be simultaneously poled in one operation.

For the rapid measurement of electrical properties, fixed electrode arrays may be constructed whose electrodes correspond to the different sample positions. The electrodes may be brought into contact with the top 18 and bottom 20 surfaces of the test materials 14' to acquire electrical data simultaneously from each of the test materials 14'.

Figure 4:
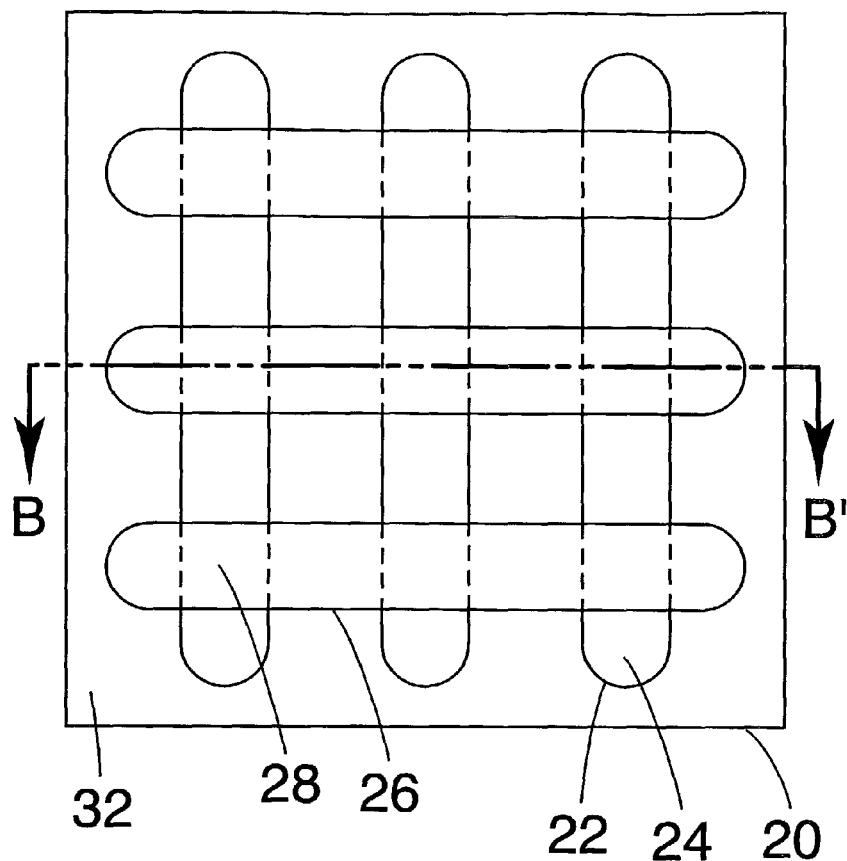
FIG. 4 illustrates a top view of a ceramic substrate defining an array of overlapping volumes of test materials of distinctive compositions in accordance with the present invention.
Figure 5:
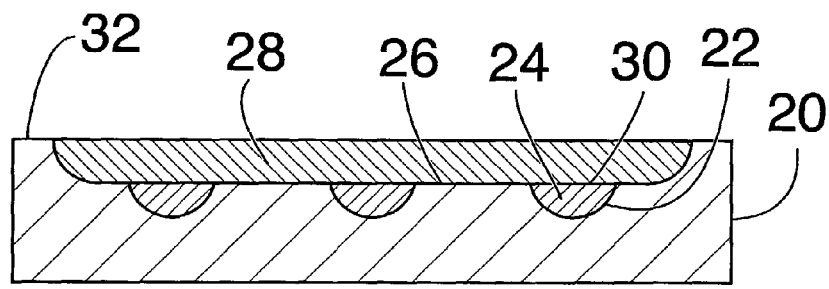
FIG. 5 is a cross section through B, B' of FIG. 4, illustrating an embodiment of the present invention where overlapping volumes of test materials are deposited into intersecting depressions in the substrate.

Referring now to FIGS. 4, 5, a substrate 20 can have cavities of various configurations according to suitability for desired testing. Cavities 22 may comprise channels in the substrate. Test materials 24 are deposited in the channels 22. Optionally using the teachings of U.S. Pat. No. 6,248,286, the composition of the test material 24 is varied along the length thereof to form a functionally graded test material 24. Moreover, intersecting channels 26 (not necessarily perpendicular as shown) can be formed and overlapping test materials 28 deposited therein, thereby creating unique compositional variations and/or interfaces at intersections 30 where the test materials overlap. The intersecting test materials 28 may optionally be functionally graded.

It will be understood that a small number of channels illustrated in FIG. 4 have been shown for simplicity and that many more channels could be used, limited only by the degree of precision which is suitable for desired testing.

It will be further understood that a third set of intersecting test materials, oriented at a different angle, for example, 45 degrees to the first two sets, could be used to create further combinations of materials. A fourth set of intersecting test materials, oriented, for example, 90 degrees to the third set, could be used to create still further combinations of materials. It is possible to have still further intersecting sets of test materials.

Figure 6:
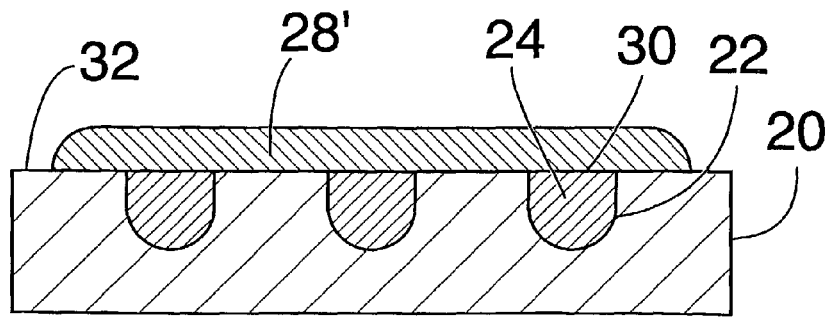
FIG. 6 is a cross section through B, B' of FIG. 4, illustrating an embodiment of the present invention where some overlapping volumes of test materials are deposited into intersecting depressions in the substrate, and other overlapping volumes of test materials are deposited on the surface of the substrate.

As shown in FIG. 6, rather than machining channels into the substrate 20, some of the test materials may be deposited in strips 28' on the surface 32 of the substrate 20. Thick-film and/or thin-film materials can be deposited and tested in conjunction with bulk test materials.

Modern electronic and electrical systems are placing increasing demands on the performance characteristics of dielectric materials for applications in bulk capacitors. Since the characteristics of the dielectric materials in thin-film form frequently differ significantly from those of bulk dielectric ceramics, the development of new materials for applications in advanced capacitors must be carried out using macroscopic specimens. The characteristics and advantages embodied in the present invention are ideally suited to the preparation of combinatorial libraries of complex dielectric materials on the macroscopic scale that is required in order to discover and optimize new compositions and multi-component compounds and composites for applications in advanced capacitors.

EXAMPLE VI

A test article is prepared in accordance with Examples I, II, and V comprising a substrate material that represents the primary phase around which systematic variations in the composition is realized through the addition and reaction of controlled quantities of one or more secondary phases for the purpose of creating a suite of dielectric compositions.

The combinatorial library described above in Example VI can also be evaluated with respect to interactions with commonly used electrode materials. Using the present invention, a factorial experiment can easily be designed wherein different dielectric regions may have different thick-film or thin-film electrode materials overprinted thereon and fired. Thus, many dielectric-electrode combinations may be simultaneously evaluated. The evaluation process may include not only electrical properties but also microscopic examination, adhesion testing, aging or lifetime tests, etc., as are well known in the field of ceramic capacitors.

In addition to their use as dielectrics for capacitors, similar mixed-oxide compositions may be formulated to have certain desired positive or negative temperature coefficients of resistivity (so-called PTC and NTC materials). The present invention is equally suitable for preparing large combinatorial libraries of such materials.

Varistor ceramics are currently widely used in devices and electrical systems that range from televisions and home computers to large electrical utility power distribution systems. Varistors provide protection for such systems against electrical surges (e.g., from lightening strikes) and overvoltages due to component failures or malfunctions. The principal component of a varistor is a bulk polycrystalline ceramic (typically ZnO) that is appropriately doped with a variety of impurities whose primary function is to alter the electrical properties of the grain boundaries. Since the fundamental mechanisms leading to varistor operation are currently not well understood, efforts are constantly underway to attempt to improve varistor performance by empirical alterations and assessments of different compositions and ceramic processing conditions.

EXAMPLE VII

A test article is prepared as in with Examples I, II, and IV. A substrate material of zinc oxide and conventional compositional modifiers is prepared with an array of cavities. Varying compositions of activator oxides, for example, $CoO$, $Cr_2O_3$ are deposited into the cavities. A combinatorial library of potential varistor compositions is produced through thermal reactions induced by firing the test plate.

Large numbers of experimental varistor compositions and other ceramic microstructures can be produced quickly and easily using the present invention. Since the functionality of varistors depends on grain boundary properties of bulk ceramics made by sintering, thin-film combinatorial methods are not as applicable in the development of new varistor materials.

Thermoelectric materials have a wide range of applications in heating and cooling as well as in the generation of electrical energy. Requirements for an efficient thermoelectric material are restrictive; a large Seebeck coefficient coupled with a high electrical conductivity and a low thermal conductivity are considered necessary. Because of their wide range of applicability, thermoelectric materials are a continuing subject of research and development whose goal is to identify more efficient practical compositions.

Recent studies have concentrated on a variety of clathrate compositions as well as Skutterudite-structure compounds. Since the properties of a high electrical conductivity and a low thermal conductivity are frequently contradictory properties, thus far, only a few practical thermoelectric materials have been identified. The present invention provides opportunity to synthesize and test a large number of materials in the form of combinatorial libraries.

Test materials can contain various dopants and/or other additives that can be synthesized by thermal reaction either ex-situ (prior to deposition of the slurry into cavities) or in-situ (following deposition of the slurry into cavities) to produce combinatorial libraries of experimental compositions. In the case of in-situ processing, additives are added to the cavities after the slurry containing major constituent is added thereto. Thus, additives can be added in progressive concentrations to achieve a combinatorial library comprising an array of test materials, each of which contains slightly more or less additive than the next test material in the library.

The development of new scintillating glasses for the detection of x-rays and gamma-rays is important in the realization of new systems for medical imaging in which the radiation dose to the patient is reduced. Such scintillators are also important to the development of new instruments for radiation monitoring, security screening, and fundamental nuclear and solid-state research. Since the processes that lead to the efficient conversion of a high-energy photon into many lower-energy photons are extremely complex, the development of new scintillators generally proceeds on a purely empirical and trial-and-error basis.

Compositions and host/dopant specimens may be prepared and evaluated in terms of luminescence, etc. in photons per MeV as well as respective response time. Since it is necessary to absorb a high-energy photon, macroscopic sample volumes are required in order to obtain accurate measurements of the overall efficiency of gamma-ray scintillator materials. The present invention is well suited to the preparation of a combinatorial library of scintillator glass base compositions and activator ions in a wide range of compositions and combinations. Known glass forming agents are incorporated into the substrate or into cavities therein to which dopant activator ions are added. The doped scintillator glass compositions are then formed by high-temperature treatments. This process creates a bulk active sample volume having dimensions that are sufficient to insure a reasonable level of absorption of an incident gamma ray by the candidate scintillator material. Such a combinatorial library can be evaluated for given x-ray and gamma ray excitation energies. Morover, scintillator decay times can be determined. Optical absorption and excitation spectra can be obtained by sequentially masking and addressing test materials in an array. The present invention may be applied to research for new and improved laser glasses and dopants, to the development of new and improved optical filter glasses, and to other types of optically active glasses such as photochromic materials.

Moreover, the invention can be used to synthesize combinatorial libraries of specialty glasses such as those that can be used for the disposal of radioactive or hazardous chemical wastes. One major goal of such an investigation would be to find glass compositions that exhibit exceptionally high chemical durability in aqueous environments. Through the availability of bulk glass samples, as opposed to thin film specimens, it is possible to study the time/temperature devitrification characteristics of such glasses and the formation of chemically unstable phases. Additionally, such a suite of glasses can be used to investigate surface layer formation and surface alteration effects under various conditions, for example, pH.

The invention is also applicable to the development of new types of optical fibers. By employing localized optical heating, it is possible to locally melt the area occupied by a given combinatorial specimens and to contact this area and pull test specimens of fiber optical components encompassing different dopants (e.g., Er for fiber-optic amplifiers). Such testing can only be done through the availability of bulk samples of glass of the type provided by the present invention and is not generally feasible using glass thin films.

The present invention can be used to synthesize a wide range of glass compositions for the purpose of developing new types of glass-to-metal seal materials. Compositional variations are employed in the specimen suite to form glasses that are tested for desired thermal expansion characteristics, appropriate hardness, chemical durability, and chemical compatibility with given materials, for example, metals, with which seals are to be made.

The present invention can also be used to screen candidate biomaterials, including glass-ceramics, for many different characteristics, including thrombogenicity, protein attachment (often a precursor to thrombogenesis), cell or bacterial adhesion, resorption rate, etc. A test library is fabricated as described in the previous examples, after which it is sterilized and introduced into contact with a suitable bone material, cartilage, cell culture medium, whole blood, serum, or any other biological tissue. After exposure for an appropriate time and under appropriate conditions, samples can be characterized by optical or electron microscopy or by any suitable analytical method to determine cell density, protein adhesion, plaque formation, biocompatibility, and other characteristics and properties.

In the development of high-temperature superconducting (HTSC) materials, a key parameter is the critical current density. Using the present invention, a substrate of "base" HTSC composition can be gelcast and then modified test materials are formed through doping with other elements or oxides. After sintering, the test article can be examined using the well-known technique of 3rd harmonic detection. For example, see J. H. Claassen, M. E. Reeves and R. J. Soulen, Jr., Rev. Sci. Instrum. vol. 62, p. 996–1004 (1991). The method involves a computer controlled scanning technique where a small probe is lifted, moved into position, and brought into contact with test material. The probe consists of two small coils wound on one another, one for excitation of shielding currents in the film and the other one as inductive pickup. The signal of the latter is fed into a lock-in amplifier. As soon as the critical current is reached, the response becomes nonlinear and a 3rd harmonic component can be easily detected. A fully automated device is commercially available from THEVA Company EM-Technology Inc., 700 Kalmia Ave., Boulder, Colo. 80304. See also www.theva.com on the Internet.

The present invention allows replication of various "bulk" processing methods. For example, a dried green test article may be further densified by cold isostatic pressing prior to sintering. Furthermore, sintering may be conducted in any appropriate atmosphere or vacuum and that various densification means may be employed such as hot isostatic pressing, hot forging, etc. Sintering may be preceded by a separate binder burnout step as is well known in the art of ceramic gelcasting. Hydrothermal processing may be employed for systems such as, for example, hexagonal ferrites, zeolites, and dielectrics, either as a final process step or as an intermediate conversion step prior to final sintering.

The present invention is applicable to most bulk ceramic and powder metallurgical methods.

The present invention can be applied to ceramic-metal composites ("cermets") and other materials that are processed by powder consolidation and sintering. Some additives may be introduced as the element thereof and converted during firing to an oxide, nitride, carbide, or the like. Compositional modifiers may be added not only as powders but also as soluble species such as metal salts depending on their desired concentrations.

The present invention can be combined in various orders and in some cases repeated. For example, one might add certain compositions to the cavities and subsequently drill smaller, preferably but not necessarily concentric cavities within the test materials to add another dimension to the variety of tests that can be performed. In another embodiment of the invention, one might add certain compositions to the cavities and subsequently drill second cavities into the substrate that overlap the first cavities to add yet another dimension to the variety of tests that can be performed.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A method of preparing a test article having an array of inorganic compositions comprising the steps of:
   a. casting a substrate slurry in a mold of a selected shape, said substrate slurry containing at least an inorganic powder, a solvent, and a polymerizable monomer;
   b. polymerizing said monomer so that said substrate slurry forms a hydrogel;
   c. drying said hydrogel to form a substantially solid ceramic green substrate;
   d. machining a plurality of cavities into at least one surface of said green substrate;
   e. rehydrating said green substrate by reintroducing said solvent;
   f. depositing test slurries into at least two of said cavities, each of said test slurries comprising at least a powder, a solvent, and a polymerizable monomer, at least two of said test slurries differing from said substrate slurry in at least one compositional characteristic, said at least two test slurries differing from each other in at least one compositional characteristic; and
   g. polymerizing said monomer in said test slurries in said cavities to form a plurality of test materials in said cavities, at least two of said plurality of test materials differing from said substrate in at least one compositional characteristic, at least two of said plurality of test materials differing from each other in at least one compositional characteristic.

2. A method in accordance with claim 1 further comprising the additional step of drying said test article to form a dried green body.

3. A method in accordance with claim 2 further comprising the additional step of sintering said green body to form a sintered body.

4. A method in accordance with claim 2 further comprising the additional step of machining at least one secondary cavity into said at least one surface of said dried green body.

5. A method in accordance with claim 4 further comprising the additional steps of:
   a. depositing a secondary test slurry into said secondary cavity, said secondary test slurry comprising at least a powder, a solvent, and a polymerizable monomer, said secondary test slurry differing from said substrate slurry in at least one compositional characteristic; and
   b. polymerizing said monomer in said secondary test slurry in said cavity to form a secondary test material in said cavity, said secondary test material differing from said substrate in at least one compositional characteristic.

6. A method in accordance with claim 5 wherein said secondary test material has an interface with at least one of said test materials.

7. A method in accordance with claim 1 wherein said cavities comprise individual wells and the spacing of said wells is sufficiently large to substantially prevent undesired interdiffusion of test materials.

8. A method in accordance with claim 1 wherein said cavities comprise individual wells and the spacing of said wells is sufficiently small to allow desired interdiffusion of test materials.

9. A method in accordance with claim 1 wherein said cavities comprise channels.

10. A method in accordance with claim 9 wherein the concentration of at least one modifying element in at least one of said test slurries is varied along the length of at least one of said channels.

11. A method in accordance with claim 9 wherein at least two of said channels intersect with each other.

12. A method in accordance with claim 1 wherein at least two of said test materials overlap.

13. A method in accordance with claim 1 wherein said test materials extend completely through said test article in one dimension.

14. A method in accordance with claim 1 wherein at least one of said test material comprises at least one material selected from the group consisting of: structural ceramics; silicon nitride; solid electrolytes; oxygen membranes; emissive materials; refractories; ferrites; dielectrics; varistors; catalytic materials; zirconia; high temperature superconductors; scintillators; phosphors; dosimeter materials; radiation resistant ceramics; and luminescent materials.

15. A method of preparing a test article having an array of inorganic compositions comprising the steps of:
   a. casting a substrate slurry in a mold of a selected shape, said substrate slurry containing at least an inorganic powder, a solvent, and a polymerizable monomer;
   b. polymerizing said monomer so that said substrate slurry forms a hydrogel;
   c. drying said hydrogel to form a substantially solid ceramic green substrate;
   d. machining a plurality of cavities into at least one surface of said green substrate;
   e. rehydrating said green substrate by reintroducing said solvent;
   f. depositing test slurries into at least two of said cavities, each of said test slurries comprising at least a powder, a solvent, and a polymerizable monomer, at least two of said test slurries differing from said substrate slurry in at least one compositional characteristic, said at least two test slurries differing from each other in at least one compositional characteristic; and
   g. polymerizing said monomer in said test slurries in said cavities to form a plurality of test materials in said cavities, at least two of said plurality of test materials differing from said substrate in at least one compositional characteristic, at least two of said plurality of test materials differing from each other in at least one compositional characteristic.

16. A method in accordance with claim 15 further comprising the additional step of drying said test article to form a dried green body.

17. A method in accordance with claim 16 further comprising the additional step of sintering said green body to form a sintered body.

18. A method in accordance with claim 15 further comprising the additional step of forming at least one secondary cavity into said at least one surface of said test article.

19. A method in accordance with claim 18 further comprising the additional steps of:
   a. depositing a secondary test slurry into said secondary cavity, said secondary test slurry comprising at least a powder, a solvent, and a polymerizable monomer, said secondary test slurry differing from said substrate slurry in at least one compositional characteristic; and
   b. polymerizing said monomer in said secondary test slurry in said cavity to form a secondary test material in said cavity, said secondary test material differing from said substrate in at least one compositional characteristic.

20. A method in accordance with claim 19 wherein said secondary test material has an interface with at least one of said test materials.

21. A method in accordance with claim 15 wherein said cavities comprise individual wells and the spacing of said wells is sufficiently large to substantially prevent undesired interdiffusion of test materials.

22. A method in accordance with claim 15 wherein said cavities comprise individual wells and the spacing of said wells is sufficiently small to allow desired interdiffusion of said test materials.

23. A method in accordance with claim 15 wherein said cavities comprise channels.

24. A method in accordance with claim 23 wherein the concentration of at least one modifying element in at least one of said test slurries is varied along the length of at least one of said channels.

25. A method in accordance with claim 23 wherein at least two of said channels intersect with each other.

26. A method in accordance with claim 15 wherein at least two of said test materials overlap.

27. A method in accordance with claim 15 wherein said test materials extend completely through said test article in one dimension.

28. A method in accordance with claim 15 wherein at least one of said test material comprises at least one material selected from the group consisting of: structural ceramics; silicon nitride; solid electrolytes; oxygen membranes; emissive materials; refractories; ferrites; dielectrics; varistors; catalytic materials; zirconia; high temperature superconductors; scintillators; phosphors; dosimeter materials; radiation resistant ceramics; and luminescent materials.

29. A method in accordance with claim 1 or 15 further comprising the additional step of evaluating at least one physical property of at least one of said test materials.

30. A method in accordance with claim 29 wherein said evaluating step comprises testing for at least one property selected from the group consisting of: optical properties; magnetic permeability; dielectric permittivity; loss tangent; microstructural features; microhardness; surface catalytic activity; biological activity; corrosion resistance; oxidation resistance; luminescence, cathodoluminescence; and scintillation.

* * * * *